(12) United States Patent
Miller

(10) Patent No.: US 8,420,593 B1
(45) Date of Patent: Apr. 16, 2013

(54) COMPOSITIONS AND METHODS FOR REGULATING MEMBRANE POTENTIAL

(76) Inventor: Landon C. G. Miller, Tuscaloosa, AL (US)

( * ) Notice: Subject to any disclaimer, the term of this patent is extended or adjusted under 35 U.S.C. 154(b) by 1137 days.

(21) Appl. No.: 11/764,398

(22) Filed: Jun. 18, 2007

Related U.S. Application Data

(60) Provisional application No. 60/814,479, filed on Jun. 16, 2006.

(51) Int. Cl.
*A01N 61/00* (2006.01)
*A61K 31/00* (2006.01)

(52) U.S. Cl.
USPC .......................................................... 514/1.2

(58) Field of Classification Search .................... 514/1.2
See application file for complete search history.

(56) References Cited

U.S. PATENT DOCUMENTS

| | | | | |
|---|---|---|---|---|
| 6,967,210 | B2 * | 11/2005 | Smith et al. .................... | 514/339 |
| 2004/0220082 | A1 * | 11/2004 | Surmeier et al. ................... | 514/2 |
| 2006/0058221 | A1 * | 3/2006 | Miller ............................... | 514/2 |
| 2006/0142179 | A1 * | 6/2006 | Miller ............................... | 514/2 |

OTHER PUBLICATIONS

Albert Lo, 20th Annual CMSC conference Jun. 4, 2005 Scottsdale AZ, Neuroprotection: A therapeutic approach for progressive disease?, Microsoft PowerPoint—Symposium 11—Lo.*
Anand et al., Current prodrug strategies via membrane transporters/receptors, Expert opin. Biol. Ther. (2002) 2(6):607-620.*
Chen et al., Differential blockage of nerve injury-induced thermal and tactile hypersensitiviy by systematically administered brain-penetrating and peripherally restricted local anesthetics, The journal of Pain, vol. 5, No. 5 (Jun. 2004): pp. 281-289.*
Ruby et al "Contributions of Kv3 channels to neuronal excitability", Ann. N. Y. Acad. Sci., Apr. 1999,vol. 868, pp. 304-343.*
"Current Research Activities." Jefferson and Magee, Regional Spinal Cord Injury Center of the Delaware Valley (believed to have been offered for sale, publicly used, and/or published prior to the filing date of this application).
Lawson, K. and N.G. McKay. "Modulation of Potassium Channels as a Therapeutic Approach." Current Pharmaceutical Design, 2006, vol. 12, pp. 459-470.
Cappelen-Smith, C., S. Kuwabara, C. Lin, I. Mogyoros, and D. Burke. "Membrane properties in chronic inflammatory demyelinating polyneuropathy." Brain, 2001, vol. 124, pp. 2439-2447.
Kanai, K., S. Kuwabara, S. Misawa, N. Tamura, K. Ogawara, M. Nakata, S. Sawai, T. Hattori, and H. Bostock. "Altered axonal excitability properties in amyotrophic lateral sclerosis: impaired potassium channel function related to disease stage." Brain, 2006, vol. 129, pp. 953-962.
Kapetanovic, I.M., W.D. Yonekawa, and H.J. Kupferberg. "The effects of anticonvulsant compounds on 4-aminopyridine-induced de novo synthesis of neurotransmitter amino acids in rat hippocampus in vitro." Epilepsy Research, 1995, vol. 20, pp. 113-120.
Yamaguchi, S. and M.A. Rogawski. "Effects of anticonvulsant drugs on 4-aminopyridine-induced seizures in mice." Epilepsy Research, 1992, vol. 11, pp. 9-16.
Devaux, J., M. Gola, G. Jacquet, and M. Crest. "Effects of K+ Channel Blockers on Developing Rat Myelinated CNS Axons: Identification of Four Types of K+ Channels." Journal of Neurophysiology, 2002, vol. 87, pp. 1376-1385.
Al-Sarraf, H., J.E. Preston, M.B. Segal. "The entry of acidic amino acids into brain and CSF during development, using in situ perfusion in the rat." Developmental Brain Research 1995, vol. 90, pp. 151-158.
Gaillard, P.J., L.H. Voorwinden, J.L. Nielsen, A. Ivanov, R. Atsumi, H. Engman, C. Ringbom, A. G. de Boer, D.D. Breimer. "Establishment and functional characterization of an in vitro model of the blood-brain barrier, comprising a co-culture of brain capillary endothelial cells and astrocytes." European Journal of Pharmaceutical Sciences 2001, vol. 12, pp. 215-222.

* cited by examiner

*Primary Examiner* — Brandon Fetterolf
*Assistant Examiner* — Jean Cornet
(74) *Attorney, Agent, or Firm* — Blue Filament Law PLLC; Avery N. Goldstein

(57) ABSTRACT

Compositions are described according to embodiments of the present invention which include a neuronal potassium channel antagonist and a neuronal sodium channel antagonist, the neuronal potassium channel antagonist and the neuronal sodium channel antagonist each conjugated to a transporter moiety to form one or more conjugates. The transporter moiety is capable of crossing the blood/brain or blood/nerve barrier such that the conjugate is delivered to the brain and/or nerve. Inventive methods of treating a demyelinating condition in a subject are described herein which include administering an effective amount of a conjugate composition of the present invention to a subject having a demyelinating condition.

4 Claims, No Drawings

COMPOSITIONS AND METHODS FOR REGULATING MEMBRANE POTENTIAL

REFERENCE TO RELATED APPLICATION

This application claims priority from U.S. Provisional Patent Application Ser. No. 60/814,479, filed Jun. 16, 2006, the entire content of which is incorporated herein by reference.

FIELD OF THE INVENTION

The present invention relates generally to compositions and methods for regulating neuronal ion channels. More specifically, the present invention relates to compositions and methods allowing transport of ion channel regulators to neuronal sites of action.

BACKGROUND OF THE INVENTION

Neuronal function is dependent on ion channels. Changes in ion channel type, localization or structure can have dramatic effects on membrane potential, conduction characteristics and action potential threshold, as well as other functional properties of neurons. The dependence of neurons on ion channel properties implicates ion channels in numerous disorders, and therapeutic treatments, of the nervous system.

Demyelinating diseases are among the most devastating diseases of the nervous system. Myelin is present in both the central and peripheral nervous systems and is largely responsible for fast salutatory conduction of nerve impulses. Demyelinating conditions are characterized by slowed or blocked conduction of nerve impulses, resulting in motor, sensory, autonomic, cognitive and emotional disturbances. Many demyelinating conditions are known, of which the most widely recognized is multiple sclerosis.

Administration of potassium channel blockers can compensate to some extent for demyelination of the axon. Treatment with mono- and/or di-aminopyridines, which are potassium channel blockers, has shown promising results in treatment of multiple sclerosis. However, treatment with a potassium channel blocker can render a neuron hyperexcitable, resulting in undesirable side effects.

There are currently no available therapies for restoring motor function in subjects with chronic spinal cord injury (SCI), a population estimated at 250,000 in the USA alone. Although many pharmaceutical products are used to treat subjects with SCI, these are almost exclusively directed to the amelioration of individual symptoms, such as pain and spasticity or the treatment of dependent conditions, such as pressure sores and bladder infections. Even a treatment with minimal effectiveness might represent a major improvement in the quality of life for subjects with SCI. Literature suggests that clinically significant improvements may be obtained with 4-aminopyridine (4-AP), a K+ channel blocker. (1,2,3,4) However, the use of 4-AP is limited by various side effects associated with central nervous system activation, which include restlessness, confusion, and infrequently reported findings of generalized tonic-clonic seizure (5,6,7).

HP184 (N-[N-propyl]-N-[3-fluoro-4-pyridinyl]-1H-3-methylindole-1-amine hydrochloride) is a sodium and potassium channel blocker. It has demonstrated activity as a voltage dependent blocker of potassium currents in PC12 cells, and as a use- and frequency dependent blocker of sodium channels. (8,9). Use-dependent sodium channel blockers act more effectively during conditions of cellular depolarization. They demonstrate little or no effect on normal neuronal signaling, but enable the blockade of sodium channels during seizures, head trauma, or ischemia. (10) Many of these agents are cerebroprotective in animal models of these pathological conditions.

In a rat compression model of spinal cord injury with mild intensity, HP184 significantly improved motor function (operationally defined as open field walking analysis) when orally administered (3, 10 and 20 mg/kg, po) to rats with an established, (25 day—post injury) spinal cord injury. This improvement was equaled by the improvement observed with 4-AP (0.6 mg/kg, ip). Drugs were administered on days 25, 26 and 27. The baseline walking analysis of the animals, prior to drug administration, showed no statistical differences across groups. Rats were sacrificed on day 30, and spinal cords were removed. Histochemical myelin staining (using Luxol Fast Blue) showed that spinal cords from the vehicle-treated group had extensive myelin loss. HP184 was then tested in a more severe injury paradigm.

In a second study, HP184 (3 mg/kg, po) significantly improved motor function in rats with long-standing (35 day—post injury) spinal cord injury of moderate intensity. Statistically significant improvement in open field walking was observed for HP184 dose groups in both studies described above.

Further, multiple dose studies in moderately injured rats (compression model) have confirmed the effectiveness of once a day oral dosing with HP184 at 3, 1, and 0.3 mg/kg. In summary, HP184 has been shown to be efficacious, as determined by the improvement in walking ability in a rat model of spinal cord injury.

However, even HP184 studies show that therapies such as 4-AP and HP184 are hindered by difficulties with transport of drugs across the blood-brain barrier and blood-nerve barrier in therapeutically effectively doses without undesirable side effects. Additionally, after a relatively small dosage range, it may become necessary to resort to direct, intraventricular delivery of such compounds in larger dosage amounts in order to avoid deleterious side effects.

Thus, there is a continuing need for compositions and methods for regulating ion channels in an individual and for allowing transport of such compositions to neuronal sites in such a manner as to increase the range of possible non-intrathecal dosage deliveries. Even just a small increase in dosage mat means many millions of health costs saved through inexpensive oral or other non-invasive delivery systems and methods.

SUMMARY OF THE INVENTION

A composition according to embodiments of the present invention includes a neuronal potassium channel antagonist and a neuronal sodium channel antagonist, the neuronal potassium channel antagonist and the neuronal sodium channel antagonist each conjugated to a transporter moiety to form one or more conjugates. The transporter moiety is capable of crossing the blood/brain or blood/nerve barrier such that the conjugate is delivered to the brain and/or nerve.

In particular embodiments, the one or more conjugates of the present invention have one of the following formulas: $X-(L)_r-Y$, $X-[(L)_r-(Y)]_s$, $X-(L)_r-[(Y)]_s$, and $X-[(L)_r-(R1-R2)]_r$. In these formulas X is a transporter moiety capable of crossing the blood brain barrier and/or the blood nerve barrier to deliver the conjugate to the brain and/or nerve, L is a linker; r is 0 or 1; Y is an ion channel antagonist, particularly a neuronal potassium channel antagonist, a neuronal sodium channel antagonist or an ion channel antagonist capable of independently inhibiting both a neuronal potassium channel and a neuronal sodium channel; s is an integer in the range of 1-10, inclusive, where R1 and R2 are each a neuronal potassium channel antagonist or a neuronal sodium channel antagonist, and at least one of R1 and R2 is a neuronal potassium channel antagonist and at least one of R1 and R2 is a neuronal sodium channel antagonist; and t is an integer in the range of 1-10, inclusive. In particular embodiments when s is 1, Y is an ion channel antagonist capable of independently inhibiting both a neuronal potassium channel and a neuronal sodium channel. In embodiments where s is an integer in the range of 2-10, inclusive, at least one Y is a neuronal potassium channel antagonist and at least one Y is a neuronal sodium channel antagonist.

In further particular embodiments, the transporter moiety is a monosaccharide or monosaccharide analog. The monosaccharide is a hexose, exemplified by D-glucose, in certain embodiments. The monosaccharide is D-mannose or D-galactose in additional embodiments of a conjugate according to the present invention.

Examples of a monosaccharide analog included as a transporter moiety in embodiments of a conjugate according to embodiments of the present invention are 2-deoxy-D-glucose and 3-O-methyl-D-glucose.

In additional embodiments of a conjugate according to the present invention, the transporter moiety is an amino acid. For example, a transporter moiety is alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, phenylglycine, norleucine, norvaline, alpha-aminobutyric acid, gamma-aminobutyric acid, citrulline, hydroxyproline, ornithine, or homoarginine.

In further embodiments, the transporter moiety is a peptide or protein. For example, a transporter moiety is insulin, nerve growth factor, leptin, insulin-like growth factor-I, or insulin-like growth factor-II. Additional peptides and proteins which may be included in a conjugate of the present invention include bradykinin, beta-endorphin, bombesin, calcitonin, cholecystokinin, an enkephalin, dynorphin, galanin, gastrin, glucagon, gonadotropin-releasing hormone, growth hormone-releasing hormone, membrane transport peptide, motilin, neurotensin, oxytocin, prolactin, neuropeptide Y, luteinizing hormone, secretin, somatostatin, substance P, a TAT peptide, thyrotropin, thyrotropin-releasing hormone, vasoactive intestinal peptide and vasopressin.

Particular transporter moieties included in a conjugate according to embodiments of the present invention are benzoate, citrate, fumarate, gluconate, lactate, malate, propionate, pyruvate and salicylate.

In a particular embodiments, the transporter moiety in a conjugate of the present invention is transferrin.

A potassium channel antagonist included in a conjugate according to embodiments of the present invention is a mono- or di-aminopyridine. For examples, 4-aminopyridine, 3, 4-aminopyridine; a pharmaceutically acceptable salt thereof; or a combination of these is optionally included in a conjugate.

A potassium channel antagonist included in embodiments of a conjugate of the present invention is an antagonist of a KCNQ1, KCNQ3/4, KCNQ2/3, BKCa, SKCa, Kv1.3, Kv1.1, Kv1.2, TASK2, or GIRK potassium channel. A potassium channel antagonist included in embodiments of a conjugate of the present invention may also be an antagonist of multiple potassium channel types.

Specific examples of potassium channel antagonists optionally included in a conjugate are linopirdine, XE991, paxilline, UCL-1684, UCL-1530, dequalinium, correolide, H-37, WIN-17317-3, CP-339818 and UK-78282. A pharmaceutically acceptable salt thereof of a potassium channel antagonist may also be included. A combination of potassium channel antagonists is optionally included in a conjugate according to embodiments of the present invention.

Specific examples of sodium channel antagonists optionally included in a conjugate are tetrodotoxin, beta-pompilidotoxin, QX-222, QX-314, riluzole and vinpocetine. A pharmaceutically acceptable salt thereof of a sodium channel antagonist may also be included. A combination of sodium channel antagonists is optionally included in a conjugate according to embodiments of the present invention.

In particular embodiments, an ion channel antagonist included in a conjugate is capable of independently inhibiting both a neuronal potassium channel and a neuronal sodium channel. A preferred ion channel antagonist included in a conjugate which is capable of independently inhibiting both a neuronal potassium channel and a neuronal sodium channel is HP184. A pharmaceutically acceptable salt of HP184 is optionally included in a conjugate of the present invention.

Inventive methods of treating a demyelinating condition in a subject are described herein which include administering an effective amount of a conjugate composition of the present invention to a subject having a demyelinating condition.

DETAILED DESCRIPTION OF THE INVENTION

A composition is provided which includes a neuronal potassium channel antagonist, a neuronal sodium channel antagonist, or a combination antagonist such as HP184. The neuronal potassium channel antagonist and the neuronal sodium channel antagonist are each conjugated to a transporter moiety to form one or more conjugates. The combination antagonist is also conjugated to a transportation moiety. In all cases, the now combined transporter moiety is capable of crossing the blood brain barrier.

The one or more conjugates included in a composition according to the present invention have a formula selected from the group consisting of: $X-(L)_r-Y$, $X-[(L)_r-(Y)]_s$, $X-(L)_r-[(Y)]_s$, $X-[(L)_r-(R1-R2)]_t$. In these formulas, X is a transporter moiety capable of crossing the blood brain barrier, L is a linker, r is 0 or 1, Y is a neuronal potassium channel antagonist, a neuronal sodium channel antagonist and/or an ion channel antagonist capable of independently inhibiting both a neuronal potassium channel and a neuronal sodium channel. Further, s is an integer in the range of 1-10, inclusive. When s is 1, Y is an ion channel antagonist capable of independently inhibiting both a neuronal potassium channel and a neuronal sodium channel. When s is an integer in the range of 2-10, inclusive, at least one Y is a neuronal potassium channel antagonist and at least one Y is a neuronal sodium channel antagonist. R1 and R2 are each a neuronal potassium channel antagonist or a neuronal sodium channel antagonist and at least one of R1 and R2 is a neuronal potassium channel antagonist and at least one of R1 and R2 is a neuronal sodium channel antagonist. The symbol t is an integer in the range of 1-10, inclusive.

A transporter moiety included in an inventive conjugate is a moiety which traverses the blood/brain barrier and/or blood/nerve barrier either by diffusion or by active or passive transport via a transmembrane transporter in order to contact a neuron or portion thereof.

Identification of a transporter moiety as capable of crossing the blood/brain and/or blood/nerve barrier to reach the brain and/or nerve is accomplished, for example, by in vitro or in vivo assay of blood/brain and/or blood/nerve barrier transport function. Such assays are known in the art, as exemplified by assays described in al-Sarraf, H. et al., Brain Res Dev Brain Res., 1995, 90:151-8 and Gaillard, P. J. et al., Eur J Pharm Sci., 2001, 12(3):215-22.

A transporter moiety includes a monosaccharide or monosaccharide analog in one embodiment of an inventive conjugate. Examples of suitable monosaccharide transporter moieties illustratively include D-glucose, D-mannose and D-galactose. Examples of suitable monosaccharide analogs illustratively include 2-deoxy-D-glucose and 3-O-methyl-D-glucose.

A transporter moiety may also include an amino acid. Amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, phenylglycine, norleucine, norvaline, alpha-aminobutyric acid, gamma-aminobutyric acid, citrulline, hydroxyproline, ornithine, and homoarginine.

A transporter moiety included in an inventive conjugate may be a peptide or protein in certain embodiments. For example, peptides and proteins useful as a transporter moiety include insulin, nerve growth factor, leptin, insulin-like growth factor-I, and insulin-like growth factor-II. The protein transferrin is a preferred transporter moiety. Further, a transporter moiety including a peptide or protein is illustratively angiotensin, bradykinin, beta-endorphin, bombesin, calcitonin, cholecystokinin, an enkephalin, dynorphin, galanin, gastrin, glucagon, gonadotropin-releasing hormone, growth hormone-releasing hormone, membrane transporter peptide, motilin, neurotensin, oxytocin, prolactin, neuropeptide Y, luteinizing hormone, secretin, somatostatin, substance P, a TAT peptide, thyrotropin, thyrotropin-releasing hormone, vasoactive intestinal peptide, or vasopressin.

In some embodiments, a transporter moiety may be benzoate, citrate, fumarate, gluconate, lactate, malate, propionate, pyruvate or salicylate.

A neuronal potassium channel antagonist included in a composition according to the present invention is preferably an antagonist of a neuronal potassium channel such as KCNQ1, KCNQ3/4, KCNQ2/3, $BK_{Ca}$, $SK_{Ca}$, Kv1.3, Kv1.1, Kv1.2, TASK2, and GIRK.

A neuronal potassium channel antagonist included in a preferred embodiment of an inventive composition is a mono- or di-aminopyridine. Exemplary suitable mono- and di-aminopyridines include 4-aminopyridine and 3,4-aminopyridine.

Additional examples of neuronal potassium channel antagonists which may be included in an inventive composition include linopirdine, XE991, paxilline, UCL-1684, UCL-1530, dequalinium, correolide, H-37, WIN-17317-3, CP-339818, and UK-78282.

Examples of neuronal sodium channel antagonists which may be conjugated to a transporter moiety illustratively include tetrodotoxin, beta-pompilidotoxin, QX-222, QX-314, riluzole and vinpocetine.

In one embodiment, an ion channel antagonist conjugated to a transporter moiety is capable of independently inhibiting both a neuronal potassium channel and a neuronal sodium channel. Such a dual function ion channel antagonist is exemplified by HP184, HP184 and additional dual function antagonists are described in U.S. Pat. No. 6,967,210.

A conjugate included in an inventive composition is produced by covalently bonding an ion channel antagonist to a transporter moiety in particular embodiments.

In a preferred embodiment, where two or more ion channel antagonists are conjugated to a transporter moiety, one or more ion channel antagonists is cleaved from the transporter moiety to yield at least one free ion channel antagonist in vivo following administration of a conjugate according to the present invention.

The simultaneous dosage of one or more conjugate compositions including at least one sodium channel antagonist and at least one potassium channel antagonist allows for more precise modulation of neuronal membrane potential. Thus, the ratio of potassium channel antagonist to sodium channel antagonist may be adjusted in view of the specific signs and symptoms of the individual patient. It is appreciated that administration of inventive conjugates having actions at multiple ion channel types are amenable to simultaneous delivery in order to provide still more refined therapeutic effects. For example, multiple potassium channel types may be targeted with multiple antagonists.

In one embodiment, an inventive conjugate is formed through an amide linkage between the transporter moiety and the neuronal potassium channel antagonist, neuronal sodium channel antagonist and/or ion channel antagonist capable of independently inhibiting both a neuronal potassium channel and a neuronal sodium channel.

Conjugation chemistries used in conjugation of a transporter moiety and an ion channel antagonist illustratively include coupling agents such as glutaraldehyde, carbodiimide, succinmde esters, benzidine, periodate, isothionate and combinations of these.

In one embodiment, an ion channel antagonist is conjugated to a transporter species via a carbodiimide cross-linker to form a conjugate having an amide linkage. Carbodiimides are zero length cross-linkers that mediate the formation of an amide or phosphoramidate linkage between a carboxylate and an amine, or a phosphate and an amine, respectively. (Chu, B., Kramer, F. & Orgel, L. (1986), "Synthesis of an amplifiable reporter RNA for bioassays," Nucleic Acids Research, 14, 5591-5603. Hoare, D. & Koshland, D. E. (1966) J. Am. Chem. Soc., 88, 2057.) They react with carboxylic acids to form highly reactive O-acylisourea compounds that are very short lived but react with nucleophiles to form an amide bond. There are several competing and nonproductive reactions, such as with water to regenerate the carboxylate group. This reaction works effectively between pH 4.5 and 7.5. Typical reaction times are 1.5-24 hours at 4-25° C. Molecules with a phosphate group such as the 5' phosphate on oligonucleotides can also react with amine-containing groups by using the carbodiimide reaction.

In an alternative embodiment, an ion channel antagonist is conjugated to a transporter species in the form of an ester or acid chloride. For example, an ion channel antagonist is reacted with a transporter moiety ester.

A protective group may be added to a transporter moiety and/or an ion channel antagonist in a process to form a conjugate according to the present invention. Such groups, their generation and use are described in Protective Groups in Organic Synthesis by T. W. Greene and P. G. M. Wuts, John Wiley & Sons, 1999.

A transporter moiety and an ion channel antagonist may be linked directly to form a conjugate. Alternatively, a linker may be bound to both a transporter moiety and an ion channel antagonist, such that these moieties are indirectly linked through the linker. A linker in simplest form includes at least two functional groups for reaction with an ion channel antagonist and a transporter moiety. A linker may be a homo-bifunctional linker or a hetero-bifunctional linker, depending on the identity of the transporter moiety and the ion channel antagonist to be conjugated. A linker may be multifunctional so as to link more than one transporter moiety and/or more than one ion channel antagonist. Suitable chemistries for a variety of potential reaction moieties are found in Comprehensive Organic Transformations, R. C. Larock, John Wiley & Sons 1999.

Thus, for example, a linker may have two carboxylate groups, two amine groups, or one amine and one carboxylate group for conjugation with a transporter moiety and an ion channel antagonist having corresponding functional groups via a carbodiimide cross-linker.

A linker may be a natural or synthetic polymer in some embodiments. For example, suitable polymers include agarose, carboxymethylcellulose, cellulose, dextran, and polyaminopolystyrene.

In embodiment in which a linker is included, the linker is chosen to limit both the molecular weight and the hydrophilicity of the linker in order to retain the ability of the conjugate to traverse the blood brain barrier. In one embodiment, a linker has about 1-20 backbone carbon atoms. However, a linker may be larger or smaller.

It is appreciated that a linker, when present, is the preferred site for the attachment of an additional species. A substituent is optionally provided pendent from the linker backbone. The substituent illustratively includes a radioactive atom, a magnetic spectroscopically active marker and an organic dye. A radioactive atom is alternatively operative as a marker in isotope studies such as positron emission tomography, single photon emission computer tomography, radiological studies and the like. Common radio-isotopes used in medical imaging illustratively include 1231, 99 mTc, and other chelated radioisotopes as detailed in U.S. Pat. No. 6,241,963. Spectroscopically active markers include NMR/MRI active contrast enhancing moieties known to the art such as gadolinium, as detailed in "Contrast Agents 1: Magnetic Resonance Imaging" (Topics in Current Chemistry, 221) by Werner Krause, Springer Verlag, Berlin, Germany. Organic dyes, while recognized to have potentially distinct NMR/MRI signatures, are provided to yield an optically active spectroscopic signature suitable for biopsy, surgical identification, or preclinical studies of tissue treated by an inventive compound.

Substituents extending from a linker may also be provided to modify the lipophilicity of an inventive conjugate for example.

A method of treating a demyelinating condition in a subject is provided according to the present invention. An inventive method includes administering an effective amount of a composition including both a neuronal potassium channel antagonist and a neuronal sodium channel antagonist.

Demyelinating conditions illustratively include immune-related demyelinating diseases such as anti-GM2 antibody syndrome, anti-MAG syndrome, anti-sulfatide antibody syndrome, chronic immune demyelinating syndrome, GALOP (Gait disorder; Autoantibody; Late-age-Onset; Polyneuropathy) syndrome, Guillain-Barré syndrome, multifocal motor neuropathy, POEMS (Polyneuropathy, Organomegaly, Endocrinopathy, Monoclonal gammopathy, and Skin changes) syndrome; toxin-related demyelination conditions such as those involving buckthorn, diphtheria, drug-related demyelination conditions such as those involving chloroquine, tacrolimus, perhexyline, procainamide, and zimeldine; hexachlorophene, sodium cyanate, and tellurium; hereditary conditions involving a demyelination component Charcot-Marie-Tooth disease, Friedrich's ataxia, lipoprotein neuropathies, porphyria, and familial amyloid neuropathies; acquired disorders involving a demyelination component such as multiple sclerosis, transverse myelitis and diabetes; and neurological injury involving a demyelination component, such as spinal cord injury or traumatic brain injury, and including diffuse axonal injury.

An inventive composition preferably includes a pharmaceutically acceptable carrier in a formulation for administration to a subject. The term "pharmaceutically acceptable carrier" as used herein is intended to refer to a carrier or diluent that is generally non-toxic to an intended recipient and which does not significantly inhibit activity of an active agent included in the composition.

An inventive composition may be administered to a subject by any of a variety of systemic and/or local routes illustratively including intravenous, oral, parenteral, intrathecal, intracerebroventricular, and mucosal.

The term "therapeutically effective amount" as used herein is intended to mean an amount of an inventive composition which is effective to alleviate or ameliorate a symptom or sign of a demyelinating condition. Exemplary signs and symptoms include tingling or numbness, weakness of the limbs, paralysis, muscle pain, abnormality of deep tendon reflexes, fatigue, abnormal sensations, difficulty breathing, swallowing and/or coughing, visual abnormalities, spacticity, cognitive abnormalities and slowed nerve conduction velocity.

A therapeutically effective amount of an inventive composition will vary depending on the particular conjugates included in the composition, the severity of demyelinating condition, and the general physical characteristics of the individual to be treated. One of skill in the art could determine a therapeutically effective amount in view of these and other considerations typical in medical practice. In general it is contemplated that a therapeutically effective amount would be in the range of about 0.001 mg/kg-100 mg/kg body weight/day, more preferably in the range of about 0.01-10 mg/kg, and further preferably in the range of about 0.1-5 mg/kg. Dosage may be adjusted depending on whether treatment is to be acute or continuing.

Compositions suitable for administration are variously formulated illustratively including as physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, and vehicles include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Such formulations are administered by a suitable route including parenteral and oral administration. Administration may include systemic or local injection, and particularly intravenous injection.

Compositions according to the present invention may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, an inventive composition is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include buffering agents. Soft and hard-filled gelatin capsules may also be prepared using such excipients.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration may include a pharmaceutically acceptable carrier and be formulated as an emulsion, solution, suspension, syrup, or elixir. In addition to the one or more conjugates of the composition, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

An inventive composition can also include adjuvants, such as wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

An ion channel antagonist included in a conjugate of the present invention may be provided as a pharmaceutically acceptable salt of the antagonist in some embodiments. The term "pharmaceutically acceptable salt" refers to a formulation that is substantially non-toxic to the individual being treated and which does not substantially inhibit the activity of an active agent being administered.

Detailed information concerning materials, equipment and processes for preparing and manufacturing various dosage forms may be found in Pharmaceutical Dosage Forms: Tablets, eds. H. A. Lieberman et al., New York: Marcel Dekker, Inc., 1989, and in L. V. Allen, Jr. et al., Ansel's Pharmaceutical Dosage Forms and Drug Delivery Systems, 8th Ed., Philadelphia, Pa.: Lippincott, Williams & Wilkins, 2004. Further examples and details of pharmacological formulations and ingredients are found in standard references such as: A. R. Gennaro, Remington: The Science and Practice of Pharmacy, Lippincott Williams & Wilkins, 20th ed. (2003); L. V. Allen, Jr. et al., Ansel's Pharmaceutical Dosage Forms and Drug Delivery Systems, 8th Ed. (Philadelphia, Pa.: Lippincott, Williams & Wilkins, 2004); J. G. Hardman et al., Goodman & Gilman's The Pharmacological Basis of Therapeutics, McGraw-Hill Professional, 10th ed. (2004

The term "subject" is used herein to refer to humans and to non-human animals such as dogs, cats, cows, horses, poultry, birds, and rodents.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A composition, comprising:
a neuronal potassium channel antagonist and a neuronal sodium channel antagonist, the neuronal potassium channel antagonist and the neuronal sodium channel antagonist each conjugated to a transporter moiety to form one or more conjugates, the transporter moiety capable of crossing the blood/brain or blood/nerve barrier; wherein said neuronal potassium channel antagonist is a mono- or di-aminopyridine and wherein the transporter moiety is a monosaccharide or monosaccharide analog.

2. The composition of claim 1 wherein the transporter moiety is D-glucose.

3. The composition of claim 1 wherein the mono- or di-aminopyridine is selected from the group consisting of: 4-aminopyridine, 3,4-aminopyridine; a pharmaceutically acceptable salt thereof; and a combination thereof.

4. The composition of claim 1 wherein the sodium channel antagonist is selected from the group consisting of: tetrodotoxin, beta-pompilidotoxin, QX-222, QX-314, riluzole, vinpocetine; a pharmaceutically acceptable salt thereof and a combination thereof.

* * * * *